(12) United States Patent
Jagadeeswaran

(10) Patent No.: US 12,310,969 B2
(45) Date of Patent: May 27, 2025

(54) ANTITHROMBOTIC COMPOSITIONS AND METHODS FOR USING SAME

(71) Applicant: UNIVERSITY OF NORTH TEXAS, Denton, TX (US)

(72) Inventor: Pudur Jagadeeswaran, Denton, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 53 days.

(21) Appl. No.: 17/866,437

(22) Filed: Jul. 15, 2022

(65) Prior Publication Data

US 2023/0054313 A1 Feb. 23, 2023

Related U.S. Application Data

(60) Provisional application No. 63/222,896, filed on Jul. 16, 2021.

(51) Int. Cl.
*A61K 31/519* (2006.01)
*A61P 7/02* (2006.01)

(52) U.S. Cl.
CPC .............. *A61K 31/519* (2013.01); *A61P 7/02* (2018.01)

(58) Field of Classification Search
None
See application file for complete search history.

(56) References Cited

U.S. PATENT DOCUMENTS 9,433,553 B2 * 9/2016 Herz ..................... A61H 9/0078

FOREIGN PATENT DOCUMENTS

WO WO-2016073956 A1 * 5/2016 ........... A61K 31/404

OTHER PUBLICATIONS

Potjewyd et al. "Degradation of Polycomb Repressive Complex 2 with an EED-Targeted Bivalent Chemical Degrader". Cell Chemical Biology. 27(1): 47-56 (Year: 2020).*
Zhang et al. "Enhancer of Zeste homolog 2 (EZH2) induces epithelial mesenchymal transition in endometriosis". Scientific Reports. 7:6804 (Year: 2017).*
Sun et al. "Loading 3-deazaneplanocin A into pegylated unilamellar liposomes by forming transient phenylboronic acid-drug complex and its pharmacokinetic features in Sprague-Dawley rats" European Journal of Pharmaceutics and Biopharmaceutics. 80: 323-331 (Year: 2012).*
Zhong et al. "A Comprehensive Map of FDA-Approved Pharmaceutical Products". Pharmaceutics. 10(4): 263 (Year: 2018).*
Raman et al. "Knockdown Screening of Chromatin Binding and Regulatory Proteins in Zebrafish Identified Suz12b as a Regulator of tfpia and an Antithrombotic Drug Target". Scientific Reports. Jul. 2021; 11:15238 (Year: 2021).*
Jagadeeswaran et al. "Chapter 9—Laser-Induced Thrombosis in Zebrafish". Methods in Cell Biology. 2011; 101:197-203. (Year: 2011).*
Holliday et al. "Choosing the Right Cell Line for Breast Cancer Research". Breast Cancer Research. 2011; 13:215. (Year: 2011).*
Chen et al. "EZH2 Inhibition Sensitizes Tamoxifen-Resistant Breast Cancer Cells Through Cell Cycle Regulation". Molecular Medicine Reports. 2018; 17:2642-2650. (Year: 2018).*
Skretting G, et al. Transcription factor FOXP3: A repressor of the TFPI gene? J Cell Biochem. 2019.
Luo C, et al. ADTRP regulates TFPI expression via transcription factor POU1F1 involved in coronary artery disease. Gene. 2020;753:144805.
Lupu C, et al., Novel protein ADTRP regulates TFPI expression and function in human endothelial cells in normal conditions and in response to androgen. Blood. 2011;118(16):4463-4471.
Arroyo A,B., et al. Regulation of TFPIα expression by miR-27a/b-3p in human endothelial cells under normal conditions and in response to androgens. Scientific Reports. 2017;7(1):43500.
Raman R, et al., RNaseH-mediated simultaneous piggyback knockdown of multiple genes in adult zebrafish. Scientific Reports. 2020;10(1):20187.
Kim S, et al., Vivo-morpholino knockdown of alphaIIb: A novel approach to inhibit thrombocyte function in adult zebrafish. Blood Cells Mol Dis. 2010;44(3):169-174.
Harte MT, et al. BRD7, a subunit of SWI/SNF complexes, binds directly to BRCA1 and regulates BRCA1-dependent transcription. Cancer Res. 2010;70(6):2538-2547.
Kikuchi M, et al. TRIM24 mediates ligand-dependent activation of androgen receptor and is repressed by a promodomain-containing protein, BRD7, in prostate cancer cells. Biochim Biophys Acta. 2009;1793(12):1828-1836.
Peng C, et al. The transcriptional regulation role of BRD7 by binding to acetylated histone through bromodomain. J Cell Biochem. 2006;97(4):882-892.
Coles AH, et al., The ING gene family in the regulation of cell growth and tumorigenesis. J Cell Physiol. 2009;218(1):45-57.
Menéndez C, et al., ING proteins in cellular senescence. Curr Drug Targets. 2009;10(5):406-417.
Margueron R, Reinberg D. The polycomb complex PRC2 and its mark in life. Nature. 2011;469(7330):343-349.
Yu J, et al. Reduced H3K27me3 leads to abnormal hox gene expression in neural tube defects. Epigenetics Chromatin. 2019;12(1):76-1.
Potjewyd F, Turner AW, Beri J, et al. Degradation of polycomb repressive complex 2 with an EED-targeted bivalent chemical degrader. Cell chemical biology. 2020;27(1):47-56.e15.
Dahm AE, et al., Estrogens, selective estrogen receptor modulators, and a selective estrogen receptor down-regulator inhibit endothelial production of tissue factor pathway inhibitor 1. BMC Cardiovasc Disord. 2006;6:40-40.
Ali Ho, et al., Oestrogen induced downregulation of TFPI expression is mediated by ERα. Thromb Res. 2014;134(1):138-143.

* cited by examiner

*Primary Examiner* — Leslie A. Royds Draper
(74) *Attorney, Agent, or Firm* — Gregory P. Einhorn; Greer, Burns & Crain, Ltd.

(57) ABSTRACT

In alternative embodiments, provided are compositions, including products of manufacture and kits, and methods, for preventing thrombotic episodes such as venous thrombosis in patients at risk, which include estrogen-treated individuals and patients with breast cancer and lung cancer, or any individual having reduced levels of TFPI protein.

10 Claims, 5 Drawing Sheets

Specification includes a Sequence Listing.

ANTITHROMBOTIC COMPOSITIONS AND METHODS FOR USING SAME

STATEMENT AS TO FEDERALLY SPONSORED RESEARCH

This invention was made with government support under DK117384, awarded by the National Institutes of Health (NIH). The government has certain rights in the invention.

REFERENCE TO SEQUENCE LISTING SUBMITTED VIA EFS-WEB

This application includes an electronically submitted sequence listing in xml format. The xml file contains a sequence listing entitled "6343.146587.xml" created on Aug. 14, 2022. The sequence listing contained in this xml file is part of the specification and is hereby incorporated by reference herein in its entirety.

TECHNICAL FIELD

This invention generally relates to medicine. In alternative embodiments, provided are compositions, including products of manufacture and kits, and methods, for preventing thrombotic episodes such as venous thrombosis in patients at risk, which include estrogen-treated individuals and patients with breast cancer and lung cancer, or any individual having reduced levels of TFPI protein.

BACKGROUND

Tissue factor pathway inhibitor (TFPI) is an anticoagulant that inhibits blood coagulation pathway enzymes VIIa and Xa. This inhibition leads to reduced fibrin formation.[1,2,3,4] Thus, increasing the TFPI levels in plasma should be useful in controlling thrombosis. The TFPI levels are due to its cumulative expression and secretion from endothelial cells, megakaryocytes, monocytes, and smooth muscle cells.[5,6,7,8,9,10,11,12,13] However, limited information is available on the regulation of TFPI levels. For example, the TFPI gene promoter has been studied by transient expression assays in human endothelial cell lines. The C-polymorphism has been shown to be linked to increased expression of TFPI mRNA. The knockdown or overexpression of FOXP3 (forkhead box P3 protein) transcription factor resulted in an increase or decrease of TFPI expression, respectively, suggesting FOXP3 might be a repressor for TFPI expression.[14] It has also been shown that androgen-dependent TFPI regulating protein (ADTRP) controls TFPI gene transcription via POU1F1, a transcriptional activator.[15] Testosterone has been shown to upregulate TFPI expression in endothelial cells.[16,17] This upregulation has been shown to be dependent on reduced levels of a microRNA that is again regulated by testosterone.[18] Despite these studies, there are no approaches to alter the levels of endogenous TFPI via transcriptional activation directly. Such an approach would be valuable in controlling thrombosis.

SUMMARY

In alternative embodiments, provided are methods for decreasing the risk of, or preventing, a thrombotic event or a thrombosis (optionally venous thrombosis) in an individual in need thereof, comprising administering a compound having a formula:

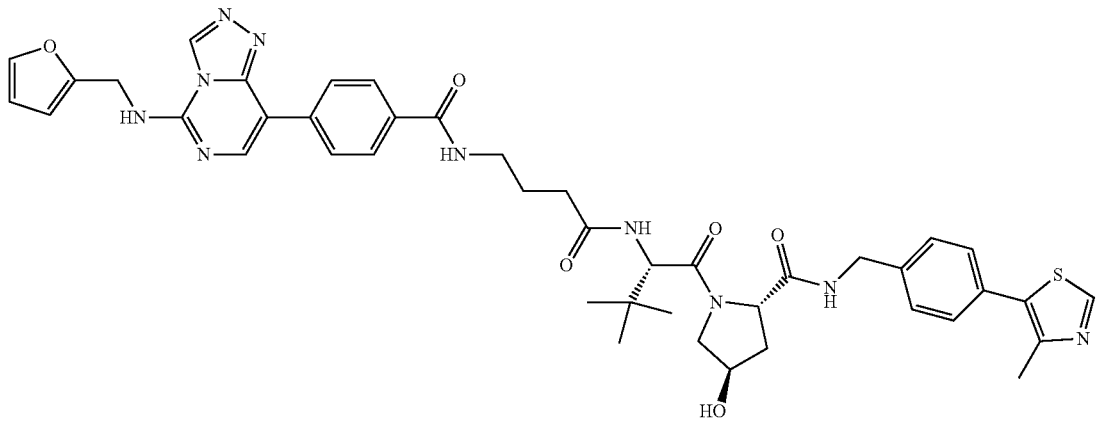

or the compound UNC6852, having CAS No. 2688842-08-0, or a salt, hydrate, solvate, tautomer, stereoisomer or deuterated isoform thereof.

In alternative embodiments of methods as provided herein:

the individual in need thereof is an estrogen-treated individual, or a patient with a cancer, optionally a breast cancer or a lung cancer, or any individual having reduced levels of Tissue factor pathway inhibitor (TFPI) protein;

the compound is formulated or manufactured as a parenteral formulation, an aqueous solution, a liposome, an injectable solution, a tablet, a pill, a lozenge, a capsule, a caplet, a spray, a sachet, an inhalant, a powder, a freeze-dried powder, an inhalant, a patch, a gel, a geltab, a nanosuspension, a nanoparticle, a nanoliposome, a microgel, a pellet, a suppository or any combination thereof, and optionally the drug delivery device or product of manufacture is or comprises an implant;

the compound is formulated or manufactured as a parenteral formulation, an aqueous solution, a liposome, an injectable solution, a freeze-dried powder, a feed, a food, a food supplement, a pellet, a lozenge, a liquid, an elixir, an aerosol, an inhalant, an adhesive, a spray, a powder, a freeze-dried powder, a patch, a tablet, a pill, a capsule, a gel, a geltab, a lozenge, a caplet, a nanosuspension, a nanoparticle, a nanoliposome, a microgel or a suppository; and/or the compound is formulated in a unit dosage amount ranging from between 0.1 mg to about 1 gram, and optionally the compound is formulated as an immediate release formulation or a controlled release formulation.

In alternative embodiments provide are kits, blister packs or packages comprising a compound having a formula:

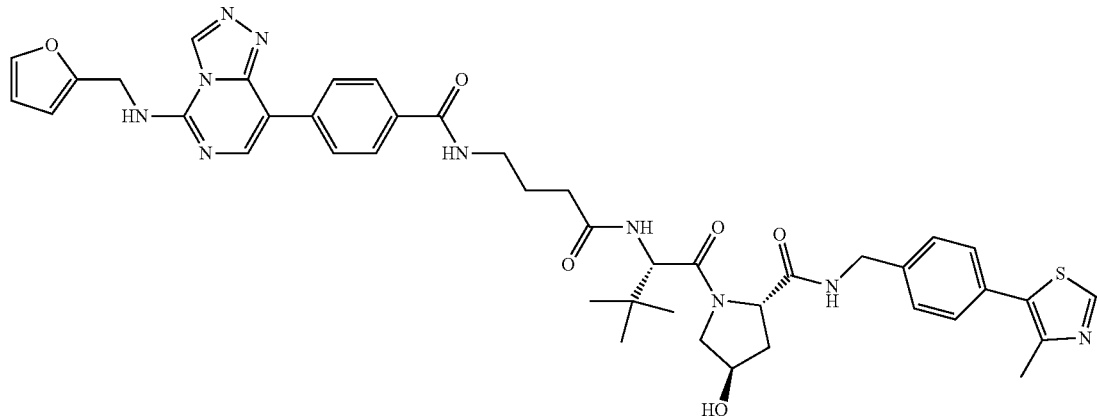

or the compound UNC6852, having CAS No. 2688842-08-0, or a salt, hydrate, solvate, tautomer, stereoisomer or deuterated isoform thereof.

and optionally the kit comprises instructions for practicing a method as provided herein.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference in their entireties for all purposes.

DESCRIPTION OF DRAWINGS

The drawings set forth herein are illustrative of exemplary embodiments provided herein and are not meant to limit the scope of the invention as encompassed by the claims.

FIG. 3A graphically illustrates a quantitative real-time PCR showing the fold change of tfpia gene expression in liver and spleen in knockdown of 5 Chromatin Binding and Regulatory Protein genes, brd7, ing2, ing3, ing4, and suz12b, with daily wild-type (WT) controls using one-way ANOVA, and the bar graphs represent a wild-type control (squared bars) and knockdowns (dotted bars) that were performed on the same day, and error bars represent mean±SD; and FIG. 3B graphically illustrates comparison of time to occlusion of the caudal vein after laser injury between wild-type control 5 dpf larvae and brd7, ing2, ing3, ing4, and suz12b knockdown larvae by one-way ANOVA, and the dot plots represent wild-type larvae (closed circles) and the knockdown larvae (closed triangles), and error bars represent mean±SD, as further discussed in detail in Example 1, below.

FIG. 4A graphically illustrates quantitative real-time PCR showing the fold change of tfpia gene expression in liver and spleen in simultaneous knockdown of 5 Chromatin Binding and Regulatory Protein genes, (brd7+ing2+ing3+ing4+suz12b) with wild-type (WT) controls using student's t-test, and the bar graphs represent wild-type control (squared bar) and simultaneous 5-gene knockdown (dotted bar), and the error bars represent mean±SD; and FIG. 4B graphically illustrates comparison of time to occlusion of the caudal vein after laser injury between wild-type control 5 dpf larvae and simultaneous 5-gene knockdown larvae (brd7+ing2+ing3+ing4+suz12b) by student's t-test, and the dot plots represent wild-type larvae (closed circles) and the knockdown larvae (closed triangles), and error bars represent mean±SD, as further discussed in detail in Example 1, below.

FIG. 5A graphically illustrates comparison of time to occlusion of the caudal vein after laser injury between wild-type control 5 dpf larvae and UNC6852-injected larvae by one-way ANOVA, and the x-axis represents four different concentrations of the UNC6852 (0.075 mM, 0.15 mM, 0.3 mM and 0.6 mM) used for larval injections, and the dot plots represent wild-type larvae (closed circles) and the knockdown larvae (closed triangles); and FIG. 5B graphically illustrates quantitative real-time PCR showing the fold change of tfpia gene expression in liver and spleen for UNC6852-injected adult zebrafish with wild-type control by student's t-test, and the concentration of UNC6852 used for adult injections (0.6 mM) is indicated beneath the bar graph, and error bars represent mean±SD, as further discussed in detail in Example 1, below.

Like reference symbols in the various drawings indicate like elements.

DETAILED DESCRIPTION

Figure 1:
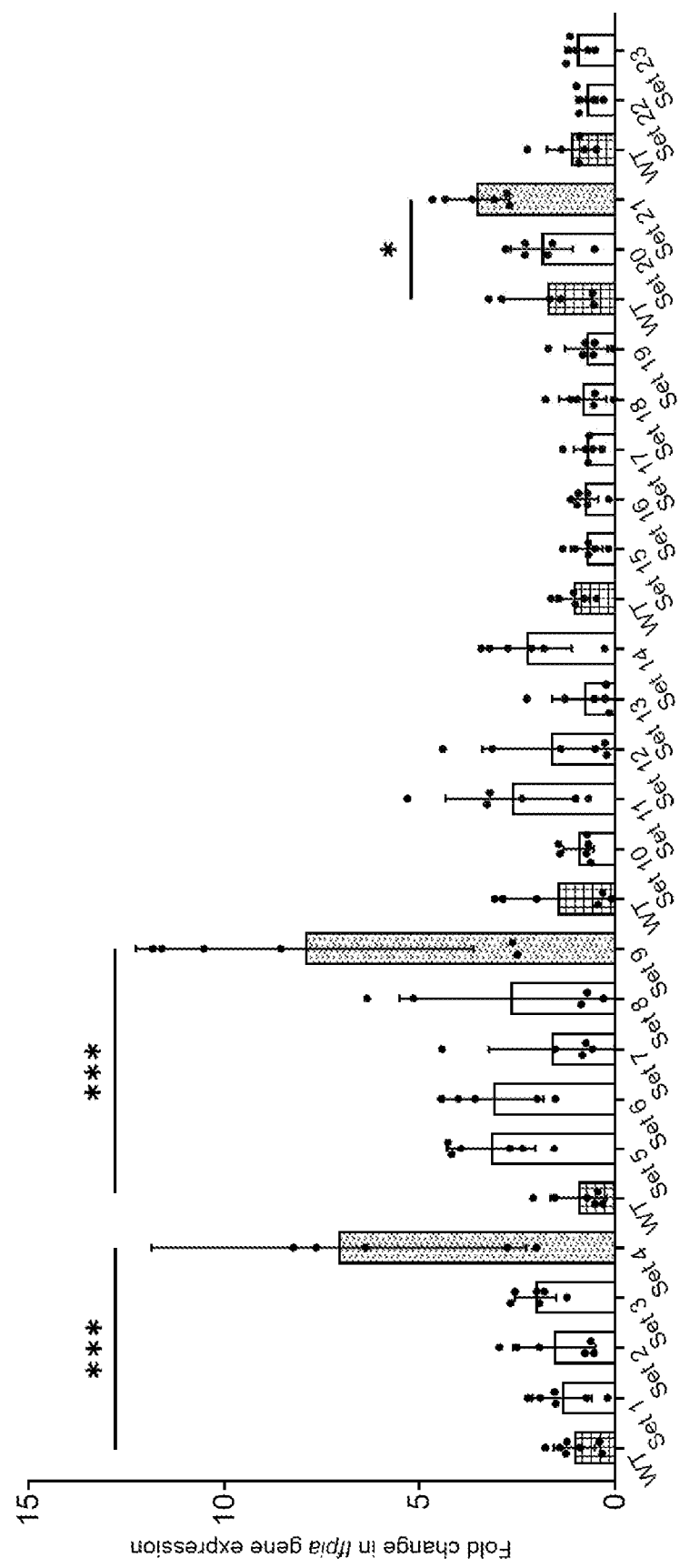
FIG. 1 graphically illustrates levels of tfpia mRNA in a primary knockdown screen of Chromatin Binding and Regulatory Proteins; the bar graphs represent daily wild-type controls (squared bars), and all knockdowns (open bars and dotted bars) to the right of each wild-type were performed on the same day, as further discussed in detail in Example 1, below.

In alternative embodiments, provided are compositions, including products of manufacture and kits, and methods, for preventing thrombotic episodes such as venous thrombosis in patients at risk, which include estrogen-treated individuals and patients with breast cancer and lung cancer, or any individual having reduced levels of TFPI protein. method for decreasing the risk of, or preventing, a thrombotic event or a thrombosis (optionally venous thrombosis) in an individual in need thereof, comprising administering the compound UNC6852, having CAS No. 2688842-08-0, or a salt, hydrate, solvate, tautomer, stereoisomer or deuterated isoform thereof.

Tissue Factor Pathway Inhibitor (TFPI) is an anticoagulant protein that inhibits factor VIIa and Xa in the coagulation cascade. It has been shown that forkhead box P3 protein is a TFPI transcriptional repressor. However, there are no studies on chromatin remodeling that control TFPI expression. We hypothesized that the genome-wide knockdowns of the Chromatin Binding and Regulatory Proteins (CBRPs) in zebrafish could identify novel tfpia gene regulators. We hypothesized that modulating Chromatin Binding and Regulatory Proteins (CBRPs) might affect the TFPI levels and could be used as a drug target.

As an initial step, we selected 69 CBRP genes from the ENSEMBL zebrafish genome database. We then performed a 3-gene piggyback knockdown screen of these 69 genes, followed by quantification of tfpia mRNA levels. The results revealed that knockdown of brd7, ing2, ing3, ing4, and suz12b increased tfpia mRNA levels. The simultaneous knockdown of these 5 genes also increased tfpia mRNA levels but not greater than that found in individual gene knockdowns. We also performed individual gene and simultaneous 5-gene knockdowns on the 5 genes in zebrafish larvae. We found that after laser injury, it took a longer time for the formation of the thrombus to occlude the caudal vessel compared to the control larvae.

We then treated the larvae and adults with a chemical UNC6852 known to proteolytically degrade polycomb repressor complex 2, where SUZ12 is a member, and observed prolongation of time to occlude the caudal vein after laser injury and increased tfpia mRNA levels in larvae and adults, respectively. In summary, our results have identified novel epigenetic regulators for tfpia and exploited this information to discover a drug that enhances tfpia mRNA levels and prolongation of time to occlusion (TTO). Thus, UNC6852 can be used as an antithrombotic drug. This approach also can be used to study the regulation of other plasma proteins, including coagulant and anticoagulant factors.

Pharmaceutical Compositions and Formulations

In alternative embodiments, compounds used to practice methods as provided herein are formulated as pharmaceutical compositions or formulations, and are formulated for administration by any or a variety of means including orally, parenterally, by inhalation spray, nasally, topically, intrathecally, intrathecally, intracerebrally, epidurally, intracranially or rectally. Pharmaceutical compositions used to practice methods as provided herein can further comprise pharmaceutically acceptable carriers, adjuvants and vehicles. In alternative embodiments, pharmaceutical compositions used to practice methods as provided herein, are formulated for parenteral administration, including administration intrathecally, intracerebrally or epidurally (into a intrathecal, intracerebral, epidural space), subcutaneously, intravenously, intramuscularly and/or intraarterially; for example, by injection routes but also including a variety of infusion techniques. Intraarterial, intrathecal, intracranial, epidural, intravenous and other injections as used in some embodiments can include administration through catheters or pumps, for example, an intrathecal pump, or an implantable medical device (which can be an intrathecal pump or catheter).

In alternative embodiments, pharmaceutical compositions used to practice methods as provided herein are formulated in accordance with a routine procedure(s) adapted for a desired administration route. In alternative embodiments, pharmaceutical compositions used to practice methods as provided herein are formulated or manufactured as lyophilates, powders, lozenges, liposomes, suspensions, solutions or emulsions in oily or aqueous vehicles, and can contain formulatory agents such as suspending, stabilizing and/or dispersing agents.

In alternative embodiments, pharmaceutical compositions used to practice methods as provided herein can be formulated as a preparation for implantation or injection. Thus, for example, the compounds can be formulated with suitable polymeric or hydrophobic materials (for example, as an emulsion in an acceptable oil) or ion exchange resins, or as sparingly soluble derivatives (for example, as a sparingly soluble salt). Alternatively, the active ingredient can be in powder form for constitution with a suitable vehicle, for example, sterile pyrogen-free water, before use. Suitable alternative and exemplary formulations for each of these methods of administration can be found, for example, in Remington: *The Science and Practice of Pharmacy*, A. Gennaro, ed., 20th edition, Lippincott, Williams & Wilkins, Philadelphia, Pa.

In alternative embodiments, pharmaceutical compositions used to practice methods as provided herein are formulated with sterile water or saline, a polyalkylene glycol such as a polyethylene glycol, an oil of synthetic or vegetable origin, a hydrogenated naphthalene and the like. In alternative embodiments, pharmaceutical compositions used to practice methods as provided herein can be formulated in or with a biocompatible, biodegradable lactide polymer, a lactide/glycolide copolymer, or polyoxyethylene-polyoxypropylene copolymers can be useful excipients to control the release of active compounds.

In alternative embodiments, pharmaceutical compositions used to practice methods as provided herein are administered using parenteral delivery systems such as ethylene-vinyl acetate copolymer particles, osmotic pumps, implantable infusion systems, intrathecal catheters, pumps and implants, and/or use of liposomes. Formulations for parenteral administration can also include glycocholate for buccal administration, methoxysalicylate for rectal administration, or citric acid for vaginal administration. Formulations for inhalation administration can contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally.

In alternative embodiments, pharmaceutical compositions used to practice methods as provided herein are administered intranasally. When given by this route, examples of appropriate dosage forms are a nasal spray or dry powder, as is known to those skilled in the art. For example, a nasal formulation can comprise a conventional surfactant, generally a non-ionic surfactant. When a surfactant is employed in a nasal formulation, the amount present will vary depending on the particular surfactant chosen, the particular mode of administration (for example drop or spray) and the effect desired.

In alternative embodiments, pharmaceutical compositions used to practice methods as provided herein are in the form of a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In alternative embodiments, sterile fixed oils are conventionally be employed as a solvent or suspending medium. For this purpose any bland fixed oil may be employed including synthetic mono- or diglycerides. In alternative embodiments, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule (ampoule) or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

In alternative embodiments, pharmaceutical compositions used to practice methods as provided herein further comprise aqueous and non-aqueous sterile injection solutions that can contain (comprise) antioxidants, buffers, bacteriostats, bactericidal antibiotics and solutes that render the formulation isotonic with the bodily fluids of the intended recipient; and/or aqueous and non-aqueous sterile suspensions, which can include suspending agents and thickening agents.

In alternative embodiments pharmaceutical compositions used to practice methods as provided herein are formulated for topical administration, for example, in the form of a liquid, lotion, cream or gel. Topical administration can be accomplished by application directly on the treatment area. For example, such application can be accomplished by rubbing the formulation (such as a lotion or gel) onto the skin of the treatment area, or by a spray application of a liquid formulation onto the application or treatment area.

In alternative embodiments, pharmaceutical compositions used to practice methods as provided herein comprise a bioimplant or a bioimplant material, and also can be coated with a compound of the invention or other compounds so as to improve interaction between cells and the implant.

In alternative embodiments, pharmaceutical compositions used to practice methods as provided herein comprise minor amounts of wetting or emulsifying agents, or pH buffering agents.

In alternative embodiments, pharmaceutical compositions used to practice methods as provided herein are formulated as a suppository, with traditional binders and carriers such as triglycerides.

In alternative embodiments, pharmaceutical compositions used to practice methods as provided herein comprise oral formulations such as tablets, pills, troches, lozenges (see, for example, as described in U.S. Pat. No. 5,780,055), aqueous or oil suspensions, dispersible powders or granules, emulsions, hard or soft capsules or geltabs, gels, jellies, syrups and/or elixirs. Compositions intended for oral use may be prepared according to any method known to the art for the manufacture of pharmaceutical compositions used to practice methods as provided herein may contain one or more agents including sweetening agents, taste-masking agents, flavoring agents, coloring agents and preserving agents, in order to provide a palatable preparation. Oral formulations can include standard carriers such as pharmaceutical grades of mannitol, lactose, starch, magnesium stearate, polyvinyl pyrrolidone, sodium saccharine, cellulose, magnesium carbonate, etc. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In alternative embodiments, formulations for oral use are hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

In alternative embodiments, pharmaceutical compositions used to practice methods as provided herein comprise aqueous suspensions comprising the active material in admixture with excipients suitable for the manufacture of aqueous suspensions. Exemplary excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (for example, lecithin), a condensation product of an alkylene oxide with a fatty acid (for example, polyoxyethylene stearate), a condensation product of ethylene oxide with a long chain aliphatic alcohol (for example, heptadecaethyleneoxycetanol), a condensation product of ethylene oxide with a partial ester derived from a fatty acid and a hexitol anhydride (for example, polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

In alternative embodiments, pharmaceutical compositions used to practice methods as provided herein comprise oil suspensions that can be formulated by suspending the active ingredient (for example, a compound of this invention) in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

In alternative embodiments pharmaceutical compositions used to practice methods as provided herein include an agent which controls release of the compound, thereby providing a timed or sustained release compound.

In alternative embodiments, pharmaceutical compositions used to practice methods as provided herein used to practice methods as provided herein, are formulated or made as a multiparticulate and/or a solid dispersion formulation, for example, as described in, for example, U.S. Patent App. Pub. No. 20080118560, for example, comprising a hydrophobic matrix former which is a water-insoluble, non-swelling amphiphilic lipid; and a hydrophilic matrix former which is a meltable, water-soluble excipient. In one embodiment, pharmaceutical compositions as provided herein used to practice the methods as provided herein are contained in tablets, pills, capsules, troches, and the like comprising any combination of a binder, for example, as a starch, polyvinyl pyrrolidone, gum tragacanth or gelatin; a filler, such as microcrystalline cellulose or lactose; a disintegrating agent, such as crospovidone, sodium starch glycolate, corn starch, and the like; a lubricant, such as magnesium stearate, stearic acid, glyceryl behenate; a glidant, such as colloidal silicon dioxide and talc; a sweetening agent, such as sucrose or saccharin, aspartame, acesulfame-K; and/or flavoring agent, such as peppermint, methyl salicylate, or orange flavoring. When the dosage unit form is a capsule, it also can comprise a liquid carrier, such as a fatty oil.

In alternative embodiments, pharmaceutical compositions used to practice methods as provided herein used to practice methods as provided herein comprise (or are contained or packaged in) unit dosage formulations having a coating, for example, a coat comprising a sugar, shellac, sustained and/or other enteric coating agents, or any pharmaceutically pure and/or nontoxic agents.

In alternative embodiments pharmaceutical compositions used to practice methods as provided herein used to practice methods as provided herein comprise (or are contained or packaged in) unit dosage formulations, wherein each different compound of the composition or product of manufacture is contained in a different layer of a pill, tablet or capsule, for example, as described in U.S. Pat. No. 7,384,653, for example, having an outer base-soluble layer and an inner acid-soluble layer. In alternative embodiments, pharmaceutical compositions as provided herein used to practice the methods as provided herein, comprise (or are contained or packaged in) unit dosage formulations, wherein each different compound of the composition or product of manufacture is contained in a liquid or a gel of different viscosity, for example, described in U.S. Patent App. Pub. No. 20050214223. In alternative embodiments, pharmaceutical compositions as provided herein used to practice the methods as provided herein, comprise (or are contained or packaged in) unit dosage formulations having reduced abuse potential, for example, as described in U.S. Patent App. Pub. No. 20040228802, for example, comprising a bittering agent, a bright deterrent/indicator dye, or a fine insoluble particulate matter.

Carriers

In alternative embodiments, pharmaceutical compositions used to practice methods as provided herein used to practice the methods as provided herein, comprise or are formulated with or as aqueous or non-aqueous solutions, suspensions, emulsions and solids. Examples of non-aqueous solvents suitable for use as disclosed herein include, but are not limited to, propylene glycol, polyethylene glycol, vegetable oils such as olive oil, and injectable organic esters such as ethyl oleate. In alternative embodiments, aqueous carriers can comprise water, ethanol, alcoholic/aqueous solutions, glycerol, emulsions and/or suspensions, including saline and buffered media. Oral carriers can be elixirs, syrups, capsules, tablets and the like.

In alternative embodiments, liquid carriers are used to manufacture or formulate pharmaceutical compositions used to practice methods as provided herein used to practice the methods as provided herein, including carriers for preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can comprise other suitable pharmaceutical additives such as solubilizers, emulsifiers, buffers, preservatives, sweeteners, flavoring agents, suspending agents, thickening agents, colors, viscosity regulators, stabilizers or osmo-regulators.

In alternative embodiments, liquid carriers used to manufacture or formulate compounds of this invention comprise water (partially containing additives as above, for example cellulose derivatives, preferably sodium carboxymethyl cellulose solution), alcohols (including monohydric alcohols and polyhydric alcohols, for example glycols) and their derivatives, and oils (for example fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

In alternative embodiments, solid carriers are used to manufacture or formulate pharmaceutical compositions used to practice the methods as provided herein, including solid carriers comprising substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (for example, povidone, gelatin, hydroxypropylmethyl cellulose), lubricant, inert diluent, preservative, disintegrant (for example, sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

In alternative embodiments, parenteral carriers are used to manufacture or formulate pharmaceutical compositions used to practice the methods as provided herein, including parenteral carriers suitable for use as disclosed herein include, but are not limited to, sodium chloride solution, Ringer's dextrose, dextrose and sodium chloride, lactated Ringer's and fixed oils. Intravenous carriers can comprise fluid and nutrient replenishers, electrolyte replenishers such as those based on Ringer's dextrose and the like. Preservatives and other additives can also comprise, for example, antimicrobials, antioxidants, chelating agents, inert gases and the like.

In alternative embodiments, carriers used to manufacture or formulate pharmaceutical compositions used to practice the methods as provided herein, can be mixed as needed with disintegrants, diluents, granulating agents, lubricants, binders and the like using conventional techniques known in the art. The carriers can also be sterilized using methods that do not deleteriously react with the compounds, as is generally known in the art.

The invention also provides articles of manufacture and kits containing (comprising) pharmaceutical compositions used to practice the methods as provided herein, including pharmaceutical compositions and formulations. By way of example only a kit or article of manufacture can include a container (such as a bottle) with a desired amount of a compound (or pharmaceutical composition of a compound) described herein. Such a kit or article of manufacture can further include instructions for using the compound (or pharmaceutical composition of a compound) described herein. The instructions can be attached to the container, or can be included in a package (such as a box or a plastic or foil bag) holding the container.

The pharmaceutical compositions used to practice the methods as provided herein can be delivered to the body or targeted to a specific tissue or organ (for example, a muscle or a brain) by any method or protocol, for example, including ex vivo "loading of cells" with pharmaceutical compositions used to practice the methods as provided herein where the "loaded cell" is the administered intramuscularly, or intrathecally, intracerebrally, or epidurally into the central nervous system (CNS), for example, as described in U.S. Pat. App. Pub. No. 20050048002.

In alternative embodiments, pharmaceutical compositions used to practice the methods as provided herein, are first lyophilized and then suspended in a hydrophobic medium, for example, comprising aliphatic, cyclic or aromatic molecules, for example, as described in U.S. Pat. App. Pub. No. 20080159984.

In alternative embodiments, pharmaceutical compositions used to practice the methods as provided herein, comprise or are formulated as pharmaceutically acceptable salts, for example, a salt of the compound UNC6852, having CAS No. 2688842-08-0, or hydrate, solvate, tautomer, stereoisomer or deuterated isoform thereof. Pharmaceutically acceptable salts can include suitable acid addition or base salts thereof. In alternative embodiments, compounds can be formulated as described in Berge et al, *J Pharm Sci,* 66, 1-19 (1977).

In alternative embodiments, pharmaceutical compositions used to practice the methods as provided herein are formulated as salts that are formed, for example, with strong inorganic acids such as mineral acids, for example hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (for example, by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Compounds of the invention also encompass salts which are not pharmaceutically acceptable, for example, a salt may still be valuable as an intermediate in a synthetic or analytical process or protocol.

In alternative embodiments, pharmaceutical compositions used to practice the methods as provided herein comprise any acceptable salt for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemi sulphate, thiocyanate, persulphate, phosphoric and sulphonic acids. Pharmaceutical compositions as disclosed herein can be prepared in accordance with methods well known and routinely practiced in the art. See, for example, Remington: *The Science and Practice of Pharmacy,* Mack Publishing Co., 20$^{th}$ ed., 2000; and *Sustained and Controlled Release Drug Delivery Systems,* J. R. Robinson, ed., Marcel Dekker, Inc., New York, 1978.

In some embodiments, pharmaceutical compositions used to practice the methods as provided herein are provided in the form of pharmaceutically acceptable salts comprising an amine that is basic in nature and can react with an inorganic or organic acid to form a pharmaceutically acceptable acid addition salt; for example, such salts comprise inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids; or optionally such pharmaceutically acceptable salts comprise sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like salts.

In alternative embodiments, pharmaceutical compositions used to practice the methods as provided herein comprise compositions manufactured under "Good manufacturing practice" or GMP, or "current good manufacturing practices" (cGMP), conditions.

Derivatized and Deuterated Compounds

In alternative embodiments, compounds used in pharmaceutical compositions used to practice the methods as provided herein are derivatized analogs, for example, metabolically blocked or otherwise altered derivatives, including deuterated, hydroxylated, fluorinated or methylated analogs or derivatives, or any combination thereof.

With regard to deuterated compounds as provided herein, or as used to practice methods as provided herein, it will be recognized that some variation of natural isotopic abundance occurs in a synthesized compound depending upon the origin of chemical materials used in the synthesis. Thus, a preparation of a compound will inherently contain small amounts of deuterated isotopologues. For compounds as provided herein, or as used to practice methods as provided herein, which include pharmaceutical preparations and formulations, when a particular position is designated as having deuterium ("-D"), it is understood that the abundance of deuterium at that position is greater than, or substantially greater than, the natural abundance of deuterium, which is 0.015%. For example, alternative embodiments of the invention comprise analogs of compounds as provided herein, or pharmaceutical compositions used to practice the methods as provided herein, having greater than 0.02%, or greater than about 0.1% deuterium. In one embodiment, the deuterium substitution, or "enrichment", occurs at a specific position or positions. In one embodiment, the deuterium enrichment is no less than about 1%, 10%, 20%, 50%, 70%, 80%, 90% or 95% or more or between about 1% and 100%.

In one embodiment, the deuterated (or otherwise substituted) compounds as provided herein, or as used to practice methods as provided herein have a slower rate of metabolism, for example, slower rate of hydroxylation, than a corresponding protonated (non-deuterated, non-substituted) compound.

Stereoisomers

In alternative embodiments, compounds used in pharmaceutical compositions used to practice the methods as provided herein exist as (comprise) individual respective stereoisomers that are substantially free from another possible stereoisomer. In alternative embodiments, the term "substantially free of other stereoisomers" as used herein means less than about 15%, 20%, 25%, 30%, 35%, 40%, 50% or 55% of other stereoisomers, or less than about 10% of other stereoisomers, or less than about 5% of other stereoisomers, or less than about 2% of other stereoisomers, or less than about 1% or less of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Methods of Administration

In alternative embodiments, compounds used in pharmaceutical compositions used to practice the methods as provided herein are administered by any or a variety of means including orally, parenterally, by inhalation spray, nasally, topically, intrathecally, intrathecally, intracerebrally, epidurally, intracranially or rectally. Pharmaceutical compositions used to practice the methods as provided herein, can be administered with pharmaceutically acceptable carriers, adjuvants and vehicles. In alternative embodiments, compounds used in pharmaceutical compositions used to practice the methods as provided herein are administered by injection routes, including a variety of infusion techniques. Intraarterial, intrathecal, intracranial, epidural, intravenous and other injections can include administration through catheters or pumps, for example, an intrathecal pump, or an implantable medical device (which can be an intrathecal pump or catheter).

In alternative embodiments compounds used in pharmaceutical compositions used to practice the methods as provided herein are administered by any known method or route, including by intranasal, intramuscular, intravenous, topical or oral, or combinations thereof, routes.

One embodiment comprises a product of manufacture comprising a pharmaceutical composition or a formulation, a blister package, a lidded blister or a blister card or packet, a clamshell, a tray or a shrink wrap, or a kit, comprising: therapeutic combinations of drugs, pharmaceutical compositions or preparations as provided herein for oral administration.

In alternative embodiments, although all ingredients can be in one blister package, a lidded blister or a blister card or packet, a clamshell, a tray or a shrink wrap, or a kit, separate ingredients can be formulated for example, for topical application, for oral or for topical application. Each ingredient can be either separately packaged, or can be formulated as one unit dose, for example, as one tube (for example, with gel, lotion etc.), ampoule, blister packette and the like.

Dosages

In alternative embodiments, compounds used in pharmaceutical compositions used to practice the methods as provided herein are formulated and administered in a variety of different dosages and treatment regimens, depending on the disease or condition to be ameliorated, the condition of the individual to be treated, the goal of the treatment, and the like, as to be routinely determined by the clinician, see for example, the latest edition of Remington: *The Science and Practice of Pharmacy*, Mack Publishing Co., supra.

In alternative embodiments, an effective amount of a compound used in pharmaceutical compositions used to practice the methods as provided herein, including a stereoisomer, salt, hydrate or solvate, is between about 0.1 mg and about 20.0 mg per kg of body weight of the individual or subject (for example, patient). In another variation, the effective amount is between about 0.1 mg and about 10.0 mg per kg of body weight of the individual or subject (for example, patient) or between about 0.1 mg and about 5.0 mg per kg of body weight of the patient. Alternately, the effective amount is between about 0.2 mg and about 2 mg per kg of body weight of the individual or subject (for example, patient).

In alternative embodiments, an effective amount of a compound used in pharmaceutical compositions used to practice the methods as provided herein (for example, as a solid dosage, such as a pill, tablet or lozenge) is between about 0.1 mg and about 2.0 mg per kg of body weight of said individual, subject or patient; or is between about 0.1 mg and about 1.0 mg per kg of body weight; or is about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, or about 1.0 mg, per kg of body weight; or an effective amount of a drug or compound as provided herein, or a composition used to practice the methods as provided herein, is about 0.1 mg, about 0.15 mg, about 0.2 mg, about 0.25 mg or about 0.3 mg per kg of body weight.

In alternative embodiment, an effective amount (for example, as a solid dosage, such as a pill, tablet or lozenge) of a compound used in pharmaceutical compositions used to practice the methods as provided herein is between about 1 mg and about 400 mg; or is a solid dosage form comprising between about 1 mg and about 250 mg; or the solid dosage form comprises between about 5 mg and about 150; or the solid dosage form (for example, as a pill, tablet or lozenge) comprises between about 1 mg and about 75; or the solid dosage form comprises about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg.

Packaging and Drug Delivery Systems

In alternative embodiments, provided are compounds, pharmaceutical compositions, formulations, preparations, formulations and/or kits, comprising combinations of ingredients, as described herein. In one aspect, each member of the combination of ingredients is manufactured in a separate package, kit or container; or, all or a subset of the combinations of ingredients are manufactured in a separate package or container. In alternative aspects, the package, kit or container comprises a blister package, a clamshell, a tray, a shrink wrap and the like.

In one aspect, the package, kit or container comprises a "blister package" (also called a blister pack, or bubble pack). In alternative embodiments, provided are therapeutic combinations, preparations, formulations and/or kits manufactured as "blister packages" or as a plurality of packettes, including as lidded blister packages, lidded blister or blister card or packets or packettes, or a shrink wrap.

In one aspect, the blister package is made up of two separate elements: a transparent or occlusive plastic cavity shaped to the product and its blister foil backing. These two elements are then sealed together into a blister strip of one or more blister with each blister an environmentally (for example moisture, pathogen, light) protected unit dose. One or more blister strips can be further joined with board material which allows the product to be package, handled, hung, displayed or shipped without damaging the blister seal and provided child resistant features. Exemplary types of "blister packages" include: Face seal blister packages, gang run blister packages, mock blister packages, interactive blister packages, slide blister packages.

Blister packs, clamshells or trays are forms of packaging used for goods; thus, provided are blister packs, clamshells or trays comprising a composition (for example, a (the multi-ingredient combination of drugs as provided herein) combination of active ingredients) as provided herein. Blister packs, clamshells or trays can be designed to be non-reclosable, so consumers can tell if a package has already opened. They are used to package for sale goods where product tampering is a consideration, such as the pharmaceuticals as provided herein. In one aspect, a blister pack as provided herein comprises a molded PVC base, with raised areas (the "blisters") to contain the tablets, pills, etc. comprising the combinations as provided herein, covered by a foil laminate. Tablets, pills, etc. are removed from the pack either by peeling the foil back or by pushing the blister to force the tablet to break the foil. In one aspect, a specialized form of a blister pack is a strip pack. In one aspect, in the United Kingdom, blister packs adhere to British Standard 8404.

In alternative embodiments, laminated aluminum foil blister packs are used, for example, for the preparation of drugs designed to dissolve immediately in the mouth of a patient. This exemplary process comprises having pharmaceutical dosage forms as provided herein prepared as an aqueous solution(s) which are dispensed (for example, by measured dose) into an aluminum (for example, alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system gives tablets an identification mark by embossing a design into the alufoil pocket that is taken up by the tablets when they change from aqueous to solid state. In one aspect, individual 'push-through' blister packs/packettes are used, for example, using hard temper aluminum (for example, alufoil) lidding material. In one aspect, hermetically-sealed high barrier aluminum (for example, alufoil) laminates are used. In one aspect, any products of manufacture as provided herein, including kits or blister packs, use foil laminations and strip packs, stick packs, sachets and pouches, peelable and non-peelable laminations combining foil, paper, and film for high barrier packaging.

In alternative embodiments, any products of manufacture as provided herein, including kits or blister packs, include memory aids to help remind patients when and how to take the drug. This safeguards the drug's efficacy by protecting each pill until it's taken; gives the product or kit portability, makes it easy to take a dose anytime or anywhere.

In alternative embodiments, pharmaceutical dosage forms as provided herein use child resistant and elderly friendly packaging, for example, packaging compliant to U.S. Government child resistant packaging regulation that requires minimal finger and grip strength. For example, in alternative embodiments foil-only containment of pills is used.

In alternative embodiments, pharmaceutical dosage forms as provided herein, are formulated or manufactured as tablets, capsules, pills or equivalents on a blister card or equivalent to track usage. By tracking usage, the blister card monitor can remind the patient and/or the primary care-giver to take medication (or that medication has been taken) at the correct time, for example, in AM and/or PM; and can facilitate discussion with health care professionals to identify and overcome barriers to adherence.

In alternative embodiments, patient usage is monitored by use of customized blister cards or equivalents using an Electronic Compliance Monitor (ECM) system (Intelligent Devices SEZC Inc. (IDI), Grand Cayman, Cayman Islands), or equivalents. For example, in alternative embodiments, the blister cards or equivalents comprise an electronic component that detects, records, safeguards and/or transmits medication removal from the blister cards or equivalents. For example, a sensor detects medication removal from the blister cards or equivalents, and this information can be transferred to a remote location for review by for example, the drug provider and/or the primary care institution or individuals. The data transfer can be by hard contact downloading of data to a transmitting and/or storage device, and can be scanned and data downloaded remotely using a radio-frequency identification (RFID) chip, tag or device or equivalent, which can be operatively connected to a computer and/or a mobile phone or other device. Radio-frequency identification uses electromagnetic fields to automatically identify and track tags attached to objects, where the tags contain electronically stored information, which in this embodiment is transmitting whether and/or when medication is removed from each compartment of the blister cards or equivalents, or by Near-Field Communication (NFC) to a NFC-enabled mobile device or mobile phone. The NFC is a set of communication protocols that enable two electronic devices, one of which is usually a portable device such as a smartphone, to establish communication by bringing them within 4 cm (1.6 in) of each other.

In alternative embodiments, a delivery systems as used in methods as provided herein can comprise use of a box to house or enclose drug delivery devices or packages, blister packages, clamshells or trays, as provided herein, where in this exemplary delivery system a week of pharmaceutical dosage form (for example, one, two or three or more tablets, pills, capsules, geltabs or equivalents) are stored on four rows, two rows for administration (for opening and self-administering by user, for example, patient) are for morning or breakfast, or AM administration, and two rows are for evening, dinnertime or PM administration; morning or breakfast, or AM administration rows are clearly separated from the evening, dinnertime or PM administration rows, and each day, and the spare dose, are arranged in column form. In alternative embodiments the blister packages, clamshells or trays are physical linked to a storage box, wherein the blister packages, clamshells or trays slide into and out of the storage box, and in alternative embodiments if needed the PM set of rows can be folded over the AM set of rows for reinsertion of the blister packages, clamshells or trays into the storage box. In alternative embodiments, the storage box comprises sensors to detect medication removal from each of the compartments (for example, which compartment is opened and when), and this information can be transferred to a remote location, for example, by Near-Field Communication (NFC) to a NFC-enabled mobile device or mobile phone, for review by for example, the drug provider and/or the primary care institution or individuals.

In any embodiment of methods as provided herein, the plasma concentration for the drug, or therapeutic combination, pharmaceutical dosage form is: (a) the trough level or trough concentration ($C_{trough}$), or the lowest concentration reached by the drug, or therapeutic combination or pharmaceutical dosage form before a second or next dose is administered, or (b) determined from blood samples taken between about 0.5 hours to 24 hours, or 4 to 12 hours, or 1, 2, 3, 4, 5, 6, 7, 8, 9, or 10 or more hours, after the last dose or administration of the drug, or therapeutic combination, pharmaceutical dosage form.

In alternative embodiments, "Individualized dosing" and "PK-guided dosing", "precision dosing" are interchangeable terms, mean administering each patient by a drug's PK properties in the patient.

In alternative embodiments, terms of "plasma concentration", "plasma drug concentration", "serum concentration", "serum drug concentration", "plasma level", "level" in the context of drug concentration, are interchangeable, and mean drug concentration in humans or animals, and measured by and interpreted by skilled in the art see Loftsson T. Essential Pharmacokinetics—1st Edition. Elsevier. 2015.

In alternative embodiments, "target therapeutic plasma drug concentration", or a similar term, is within the therapeutic plasma range, optionally about the mid-point of a therapeutic level range of plasma concentration. For example, if the therapeutic concentration, for example, the effective or efficacious plasma concentration range, for treating a disease as provided herein is between 1000 ng/ml to 1400 ng/ml, the target therapeutic plasma drug concentration can be about 1000 ng/ml, about 1300 ng/ml, or optionally the mid-point about 1200 ng/ml.

In alternative embodiments, therapeutic in the context of plasma concentration means effective or efficacious in treating a medical condition(s).

Products of Manufacture and Kits

Provided are products of manufacture and kits comprising the compound UNC6852, having CAS No. 2688842-08-0, or a salt, hydrate, solvate, tautomer, stereoisomer or deuterated isoform thereof, for practicing methods as provided herein; and optionally, products of manufacture and kits can further comprise instructions for practicing methods as provided herein.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About (use of the term "about") can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 75%, 80%, 85%, 90%, 91%, 92%, 93%, 94%, 95%, 96%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (2012) Molecular Cloning: A Laboratory Manual, 4th Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1: Knockdown Screening of Chromatin Binding and Regulatory Proteins Identified SUZ12 as a Regulator of TFPI and an Antithrombotic Drug Target This example demonstrates that methods and compositions as provided herein are effective anti-thrombotic agents.

We used the zebrafish model to identify Chromatin Binding and Regulatory Proteins (CBRPs) that are involved in tfpia gene expression. We chose 69 CBRP genes that have human orthologues from the ENSEMBL database and performed a knockdown screen of these genes in adult zebrafish, and measured tfpia mRNA levels by qRT-PCR. This screen revealed knockdown of brd7, ing2, ing3, ing4, and suz12b genes individually, increased tfpia mRNA levels. The simultaneous knockdown of these 5 genes in zebrafish larvae also showed prolongation of time to occlusion (TTO) of the caudal vein that is comparable to results of individual gene knockdowns. The treatment of the zebrafish adults and larvae with a SUZ12 inhibitor recapitulated the results of suz12knockdown. In conclusion, our results showed knockdown of brd7, ing2, ing3, ing4, and suz12b increased tfpia mRNA levels, and SUZ12 inhibitor gave an antithrombotic phenotype. Thus, this epigenetic approach could be used to control coagulation factors.

Materials and Methods

All methods were carried out in accordance with University of North Texas guidelines and regulations. The study was carried out in compliance with the ARRIVE (Animal Research: Reporting of In Vivo Experiments) guidelines. All experiments with zebrafish were approved by the University of North Texas-Institutional Animal Care and Use Committee.

Zebrafish Aquaculture

Wild-type (WT) zebrafish were obtained from Ekkwill Tropical Fish Farm, Gibsonton, FL, and were maintained in the recirculating freshwater system at 28° C. (82° F.), pH 7.6 and supplemented with Instant Ocean. The fish were kept under a 14:10 hours Light: Dark Cycle and were fed with live brine shrimp and fish flakes. One female and one male were placed in a breeding tank and separated by a divider for breeding. The following morning, the divider was removed once the lights get turned on. The embryos were transferred to embryonic E3 medium (5 mM NaCl, 0.17 mM KCl, 0.33 mM $CaCl_2$, and 0.33 mM $MgSO_4$, pH 7.2) in small plastic containers and the hatched larvae were used in further experiments.

Piggyback Knockdown and Vivo Morpholino (VMO) Hybrid Preparation cDNA sequences for 69 CBRPs in zebrafish were obtained from ENSEMBL GENOME BROWSER™, and using primer 3 software, a gene-specific antisense oligonucleotide (ASO) within the coding sequence was designed. We divided these primers into 23 sets for 3-gene knockdowns. For each set of 3 mRNAs, 3 antisense oligonucleotides (ASOs) were designed (Supplementary Table S1). To these ASOs, at their 3'-ends, 3 oligonucleotides, 5'-TATAAAT-3', 5'-TAACTGA-3', and 5'-TAAGAGG-3' were added respectively. For individual gene knockdowns, for each ASO, at its 3'-end, 5'-TATAAATTGTAACTG-3' (SEQ ID NO:1) was added. The oligonucleotides were purchased from Invitrogen, Grand Island, NY A VMO with a sequence 5'-CCTCTTACCTCAGTTACAATTTATA-3' (SEQ ID NO:2) was purchased from Gene Tools LLC, Philomath, OR For 3-gene knockdowns, the piggyback hybrid was prepared by mixing 2.5 µl of 0.5 mM VMO with 0.84 µl of each of 3 ASOs (1.5 mM of each ASO), and 0.5 mM of 10× oligo-hybridization buffer (10× OB) containing 500 mM NaCl, 10 mM Tris-HCl (pH 8.0), and 1 mM EDTA (pH 8.0) was added. For 5-gene knockdowns, the hybrid was prepared by mixing 2.5 µl of 1 mM VMO with 0.5 µl of each of 5 ASOs (2.5 mM of each ASO), and 0.5 µl of 10× OB was added.[19] For individual gene knockdowns, the hybrid was prepared by mixing 2.5 µl of 0.5 mM VMO with 2.5 µl of 0.5 mM of ASO, and 0.5 µl of 10× OB was added. The hybrid mixtures were heated to 94° C. for 5 minutes and slowly cooled to room temperature using a Takara PCR Thermal Cycler (Takara Bio, Mountain View, CA).[19]

Zebrafish Injections

Adult zebrafish was placed on its lateral side on a clean paper towel, head covered with a wet KIMWIPE™. The skin was then gently wiped with a dry Kimwipe, and 5 µl of the above piggyback hybrid or 1×PBS was then injected intravenously using a 27G1$^{1/4}$ needle as described previously.[19][20] Three dpf larvae were injected with the above hybrid using micro-capillary injection needles (David Kopf Instruments, Tujunga, California, USA) prepared by a pipette puller. The needle tip was then clipped using forceps, loaded with 5 µl of either the above hybrid or 1×PBS. The larvae were injected with 8 nl of the reagent intravenously using PICOSPRITZER III™ (Parker Precision Fluidics, Hollis, NH) and a micromanipulator under an Olympus inverted microscope as described previously.[21] After injection, the larvae were transferred to E3 medium in a plastic container at 28° C. and incubated for 48 hours.

UNC6852 (MedChem Express, Monmouth Junction, NJ), in 10% DMSO in saline were prepared at four different concentrations (0.075 mM, 0.15 mM, 0.3 mM and 0.6 mM). Eight nl of each of these solutions was injected into the 5 dpf larvae and incubated for 2 hours. For controls, 10% DMSO in saline was injected. For adult fish injections, 5 µl of 0.6 mM UNC6852 was injected intravenously and incubated for 6 hours.

RNA Extraction

Adult zebrafish were first anesthetized using 1 mM Tricaine in E3 medium. After 2 minutes, once the zebrafish flips on its side, it was removed from the medium, and an incision was made in the ventral surface from the anal pore up to the gills using a pair of scissors. The visible liver and spleen were retrieved using a pair of forceps. To this 15 mg tissue, 150 µl of TRI Reagent (Sigma-Aldrich, St. Louis, MO) was added, and homogenized using PRO200 MULTI-GEN 7XL™ Homogenizer (PRO Scientific Inc., Oxford, CT) for 1 minute. After incubating the homogenate for 10 minutes, 15 µl of 1-bromo-3-chloropropane was added and centrifuged for 15 minutes at 10,000×g. The aqueous phase was transferred into another tube, and 200 µl of isopropanol was added. After incubating for 10 minutes, the sample was centrifuged again. The pellet obtained was finally washed with 75% ethanol and suspended in nuclease-free water, and the RNA was stored at −80° C. for future use.

Quantitative Real-Time PCR (qRT-PCR)

To 1 µl of the liver and spleen RNA (1 µg/µl), 4 µl of QSCRIPT™ (gScript™) cDNA SUPERMIX™ (Quanta Bio, Beverly, MA) and 15 µl of nuclease-free water were added. This mixture was subjected to the following cycles, 25° C. for 5 minutes, 42° C. for 40 minutes, and 85° C. for 5 minutes, and finally held at 4° C. to generate cDNA. One µl of this cDNA was amplified using 1 µl of 25 µM of each of the qRT-PCR tfpia primers (forward primer: 5'-CTCC-CAACCAGCTAAACAGG-3' (SEQ ID NO:3) and reverse primer: 5'-GCGAAAGACTTGACATCTGC-3' (SEQ ID NO:4)) and 1 drop of 1-Drop PCR Mix. For control experiments, we used β-actin primers (forward primer: 5'-TCTCTTGCTCCTTCCACCAT-3' (SEQ ID NO:5) and reverse primer: 5'-CATCGTACTCCTGCTTGCTG-3' (SEQ ID NO:6)). One µl of the amplified PCR products (cDNA) was checked using 1.2% agarose gel electrophoresis. Subsequently, 1 µl of the above cDNA sample was mixed with 5 µl of PowerUp SYBR GREEN MASTERMIX™ (Thermo Fisher Scientific, Grand Island, NY), 0.2 µl of each of the qRT-PCR primers, and 3.6 µl of nuclease-free water. qRT-PCR was performed using this mixture for 45 cycles (ViiA 7 by Life Technologies, Applied Biosystems, Grand Island, NY). The data were collected for 6 individual WT samples as duplicates for their Ct values for both β-actin and tfpia gene expression, and the average of the duplicates was used as Ct values for each WT sample. The ΔCt values for WT samples were calculated as a difference between Ct values of β-actin and tfpia. The average ΔCt value for WT was then calculated. Subsequently, from each ΔCt value, the average ΔCt value was subtracted, and the resulting ΔΔCt value was used to calculate fold change for each of the 6 individual samples using the formula $2^{-\Delta\Delta Ct}$ representing the change in tfpia gene expression relative to β-actin. Similarly, in the knockdown samples, from each ΔCt value, the average ΔCt value of the WT was subtracted, and the resulting ΔΔCt value was calculated, followed by the calculation of fold change.

Laser-Induced Venous Thrombosis

For laser-induced venous thrombosis, 5 dpf larvae were transferred into a 1.5 ml Eppendorf tube containing 0.5 ml E3 medium followed by the addition of 10 µl of 10 mM MS222. After 2 minutes of anesthesia, 0.5 ml of 1.6% low melting agarose at 37° C. was added to the Eppendorf tube, and the contents were mixed gently by pipetting up and down using a transfer pipette. The contents were then poured along with the larvae into a chamber made using the rectangular rubber gasket by pressing it on to a thin coat of petroleum jelly on a microscopic slide. The larvae were adjusted with a pipette tip such that they were lying on their lateral sides. The slide with the larvae was focused with a 20× objective of the Nikon OPTIPHOT™ fluorescence microscope. The pulsed nitrogen laser with a wavelength of 445 nm, routed through the coumarin-440 dye (Micro Point Laser, Stanford Research Systems Inc., Sunnyvale, CA), was delivered at 10 hits per cycle through the fluorescence port to hit the mid-region in the caudal vein located in the 5$^{th}$ somite posterior to the anal pore.[22] TTO of the vessel was measured as the time taken to occlude the vessel from the time the laser hits the vessel until the vessel completely occludes. If the vessel did not occlude until 60 seconds, TTO was recorded as 60 seconds.

Statistical Analysis

Statistical analysis was performed using GRAPHPAD PRISM VERSION 9.0.0™, GRAPHPAD SOFTWARE™, San Diego, California, USA. Statistical significance was assessed by one-way ANOVA followed by Dunnett's multiple comparison test or student's t-test. p-value less than (<) 0.05 was considered significant.

Results

Figure 2:
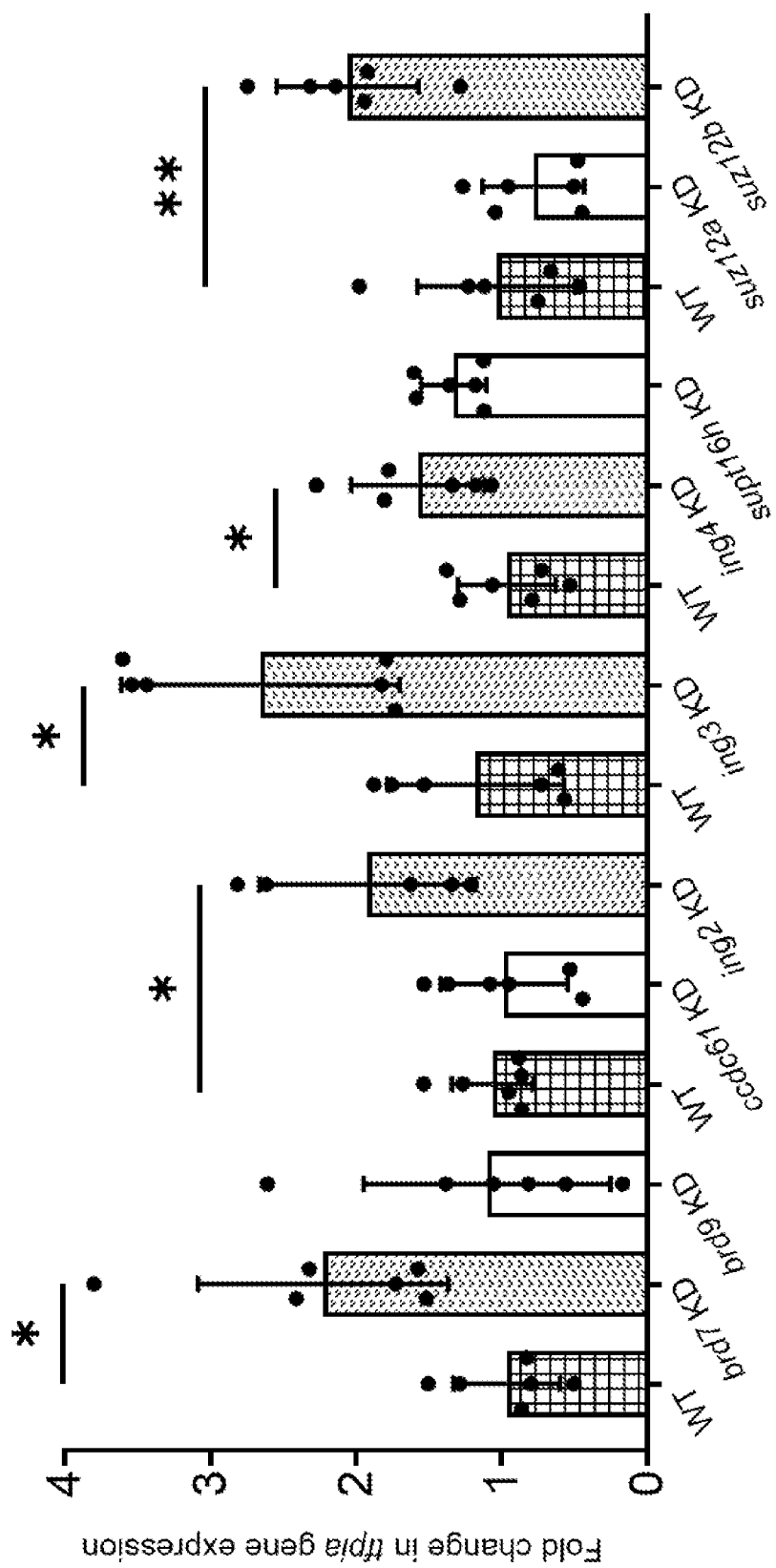
FIG. 2 graphically illustrates levels of tfpia mRNA in a secondary knockdown screen of Chromatin Binding and Regulatory Proteins, where quantitative real-time PCR show the fold change of tfpia gene expression in liver and spleen in knockdown of 9 Chromatin Binding and Regulatory Protein genes, brd7, brd9, ccdc61, ing2, ing3, ing4, supt16h, suz12a, and suz12b, with daily wild-type (WT) controls using one-way ANOVA; and the bar graphs represent daily wild-type controls (squared bars), and all knockdowns (open bars and dotted bars) to the right of each wild-type were performed on the same day and error bars represent mean±SD, as further discussed in detail in Example 1, below.
Figure 3B:
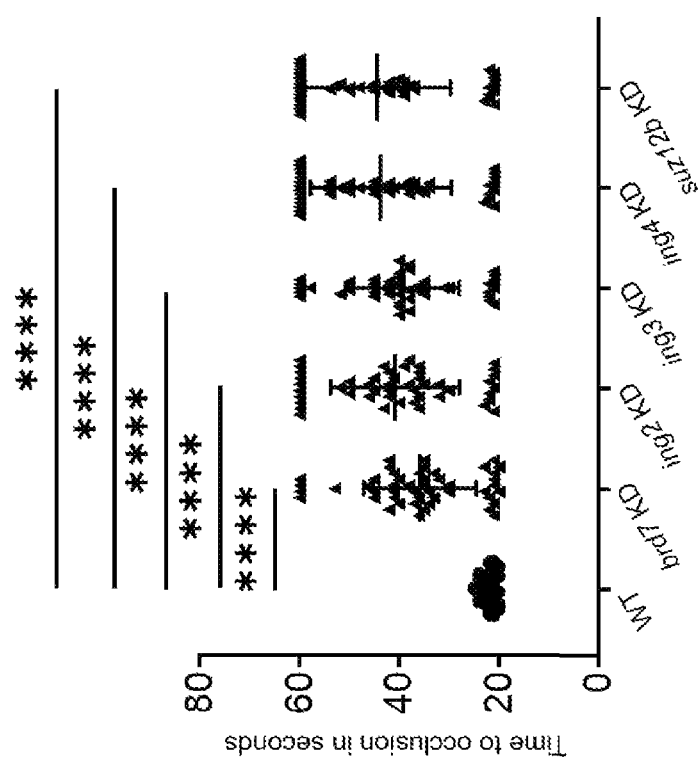
FIG. 3A-B graphically illustrate tertiary knockdown screen of genes obtained from the secondary knockdown screen in adults as well as in larvae.
Figure 3A:
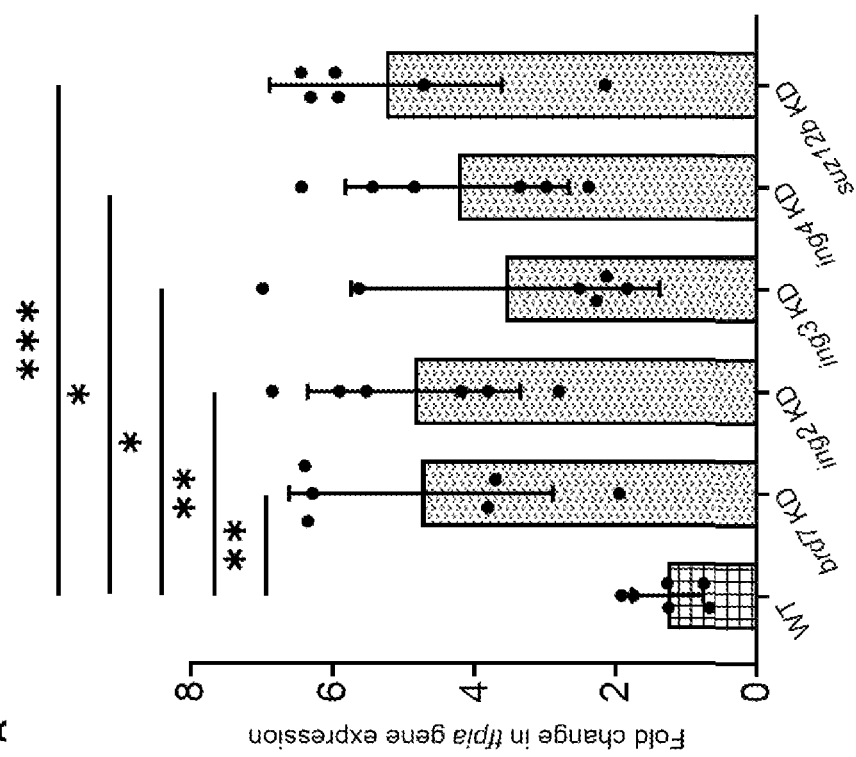

To identify the CBRPs involved in tfpia gene expression, we selected 69 CBRP genes from the single-cell RNAseq analysis of zebrafish thrombocyte transcripts performed by Weam Fallatah in our laboratory (manuscript under preparation). The above 69 CBRP mRNAs were divided into 23 sets for a 3-gene knockdown. For each set of 3 mRNAs, 3 ASOs were designed with 3 different heptamer sequences at their 3'-ends, such that these heptamer sequences will form hybrids with a VMO. We then hybridized each set of 3 ASOs with one VMO and injected the piggyback hybrid into the zebrafish intravenously. PBS-injected WT was used as a control. We used 6 adult zebrafish for each of the WT control and experimental set. Forty-eight hours later, RNA was isolated from the liver and spleen of each of the WT and piggyback hybrid-injected fish. This RNA was subjected to qRT-PCR using tfpia primers to check for the tfpia gene expression levels. β-actin was used as an internal control. In our primary screening, we identified that knockdown of 3 sets of mRNAs (Set 4, Set 9, and Set 21), corresponding to 9 individual genes, brd7, brd9, ccdc61, ing2, ing3, ing4, supt16h, suz12a, and suz12b, showed an increase in tfpia expression (FIG. 1). In our secondary screen, 9 genes from the above 3 sets were subjected to individual gene knockdowns and checked for tfpia gene expression using qRT-PCR. Out of 9 genes, 5 genes, brd7, ing2, ing3, ing4, and suz12b, after knockdown, showed an increase in tfpia mRNA levels (FIG. 2). The above results of enhanced tfpia gene expression due to the knockdown of each of the 5 genes were subjected to the tertiary screen by knocking down these 5 genes individually. We found that each of the 5 genes showed increased tfpia expression after knockdown shown by qRT-PCR (FIG. 3a). To confirm the adult knockdown results in larvae, we injected the piggyback hybrid for each of the above 5 genes individually into 3 dpf larvae. PBS-injected 3 dpf WT larvae were used as a control. We used 50 zebrafish larvae for each of the WT control and experimental set. Forty-eight hours post knockdown, laser-induced venous thrombosis was performed on 5 dpf larvae. The piggyback hybrid-injected larvae showed prolonged TTO compared to PBS-injected WT control larvae (FIG. 3b).

Figure 4A:
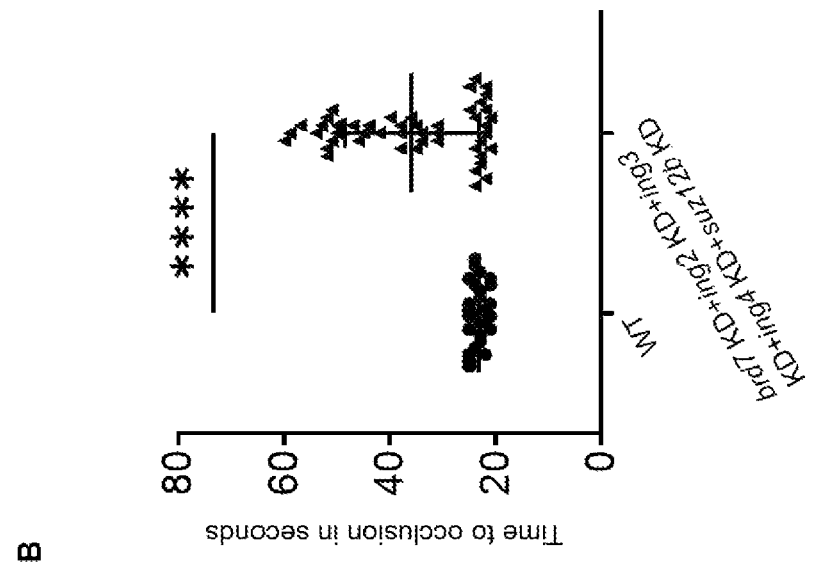
FIG. 4A-B graphically illustrate simultaneous 5-gene knockdowns in adults and larvae.
Figure 4B:
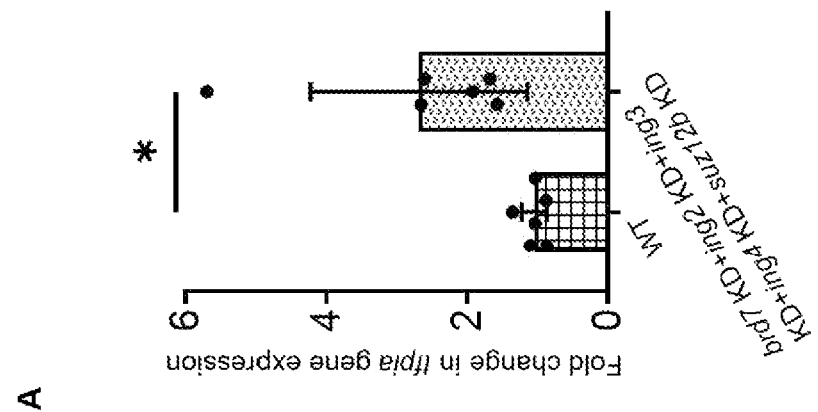

To examine the effects of simultaneous knockdown of all these 5 genes, we prepared 2 sets of piggyback hybrids with 3 ASOs in one set and 2 ASOs on the other set. We then mixed these 2 sets of 5 ASOs with one VMO (2× concentration) to prepare the final piggyback hybrid of 5 ASOs and used that in simultaneous 5-gene (brd7, ing2, ing3, ing4, and suz12b) knockdown experiments. The results showed increased tfpia gene expression in the above 5-gene knockdowns (FIG. 4a). We also performed laser-induced thrombosis after simultaneous knockdown of all 5 genes together (brd7+ing2+ing3+ing4+suz12b). The results showed a prolonged TTO as seen in individual gene knockdown experiments (FIG. 4b).

Figure 5B:
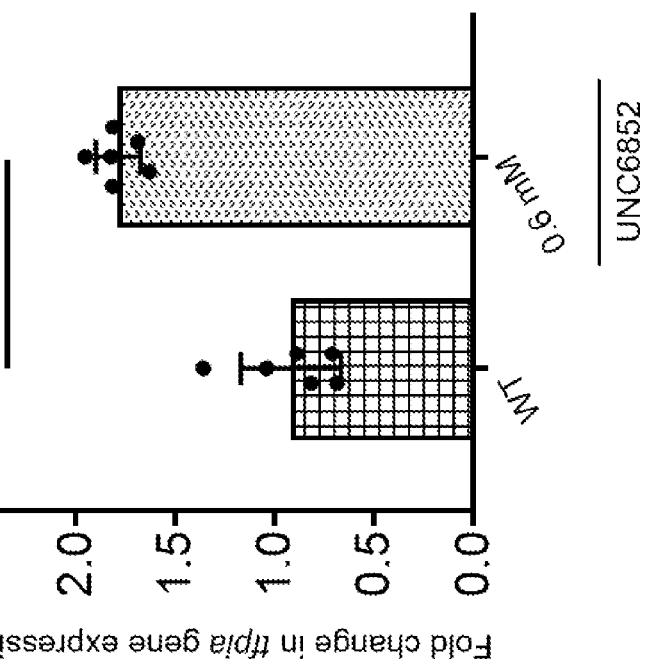
FIG. 5A-B graphically illustrate treatment of zebrafish larvae and adult with a PRC2 inhibitor, UNC6852.
Figure 5A:
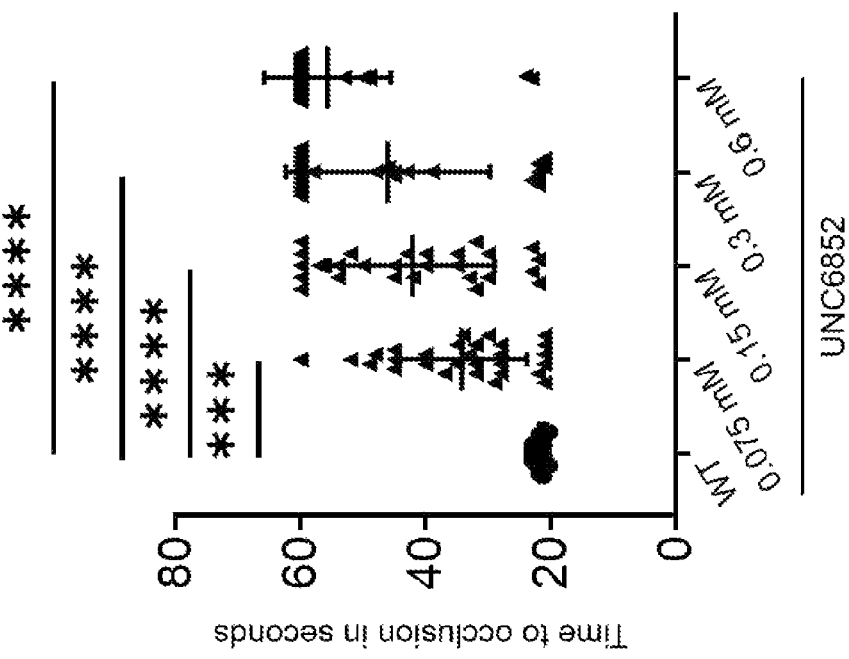

To check whether we can inhibit CBRPs encoded by the 5 genes identified above, we searched for commercially available chemical inhibitors for these proteins. We found UNC6852 as an inhibitor for polycomb repressor complex 2 (PRC2), where SUZ12 is a member. To test whether UNC6852 inhibits PRC2 and yields results similar to the knockdown of suz12b, we injected intravenously 5 dpf larvae with 4 different concentrations of the UNC6852. After 2 hours, we subjected these larvae to laser-induced venous thrombosis. We found a dose-dependent prolongation of TTO in the above larvae (FIG. 5a) compared to control larvae and also found the maximal prolongation of TTO was at 0.6 mM of UNC6852. To test whether this inhibitor enhances tfpia mRNA levels, we injected the adult fish with 5 µl of 0.6 mM of UNC6852 and found increased tfpia mRNA levels 6 hours post-injection (FIG. 5b).

Discussion

In this study, we performed simultaneous 3-gene knockdowns of 69 genes encoding CBRPs and tested their effects on tfpia gene expression. We found 5 genes when they are knocked down individually, resulted in increased tfpia mRNA levels. qRT-PCR was chosen as the assay for identifying regulators because it is a sensitive assay for studying mRNA levels. Since there is internal control, this assay to monitor tfpia levels is robust and reliable. Thus, the use of qRT-PCR to screen 23 sets of genes was relatively easy. brd7, ing2, ing3, ing4, and suz12b genes were identified in our screen as regulatory genes controlling the tfpia.

BRD7 is a member of the bromodomain-containing protein family, which plays an important role in chromatin remodeling, transcriptional regulation, and cell signaling. BRD7 both positively and negatively regulates the transcription of a number of genes such as ERα and the androgen receptor genes, respectively.[23][24] It has been shown that BRD7 binds to BRCA1, and this binding facilitates BRCA1 to be recruited to the OCT1 protein to the promoter region of ERα. Thus, BRD7 positively regulates ERα, which in turn decreases the transcription of TFPIα. Thus, the lack of Brd7 in zebrafish negatively regulates ERα and thus increases the transcription of tfpia. In addition, BRD7 has been shown to bind to acetylated histones and participate in chromatin remodeling.[25] Our results show that tfpia transcription is enhanced when brd7 transcripts are reduced. Thus, by both the above mechanisms, Brd7 appears to be a repressor for tfpia gene transcription.

The ING (inhibitor of growth) family of proteins in humans are classified as tumor suppressors involving transcriptional regulation of genes through the p53 pathway and chromatin regulation.[26] Loss of these factors could lead to cellular senescence and cancer involving mechanism such as cell proliferation, apoptosis, and DNA repair.[26][27] Our observation that the knockdown of ing2, ing3, and ing4 resulted in an increase in tfpia gene transcription suggests that the ING family of proteins are also repressors for tfpia gene and probably involves chromatin regulation.

SUZ12 (Suppressor of Zeste 12) is a member of PRC2, which consists of 2 additional proteins, a non-enzymatic EED (Embryonic Ectoderm Development) and a methyltransferase EZH2 (Enhancer of Zeste Homolog 2). The PRC2 complex is responsible for the methylation of histone H3 resulting in gene repression.[28] Loss of Suz12 in mice led to loss of H3 methylation and resulted in increased expression of Hoxa cluster genes.[29] Our results showed knockdown of suz12b resulted in increased tfpia expression. These results are also in line with our observations of enhanced transcription of tfpia in the presence of UNC6852, a SUZ12 inhibitor.[30]

Surprisingly, the simultaneous knockdown of these 5 genes did not result in a greater expression of tfpia than that shown by individual gene knockdowns. This is possible because the individual gene knockdowns might have already reached a threshold for tfpia expression. For example, Brd7, Ing family of proteins, and Suz12 are all repressors for tfpia gene transcription. Interestingly, the mechanism by which Brd7 suppresses tfpia gene transcription is by binding to acetylated histones. Ing proteins repress the gene transcription via p53. Suz12 is involved in the methylation of histones and thereby represses tfpia gene transcription. Thus, since the loss of each of these three types of regulators is involved in the reversal of the repression phenotype via different mechanisms on probably a similar region in the tfpia promoter, the loss of repression by Brd7 may result in negating the loss of repression by Suz12 or Ing proteins and vice versa. Thus, the knockdown of all these regulators together may not result in enhanced loss of repression.

Even though the knockdown of the above 5 repressors resulted in increased tfpia mRNA levels, we cannot rule out whether these knockdowns are directly affecting tfpia gene expression or whether they have an indirect effect via the expression of an activator for tfpia gene promoter. Future studies should resolve this issue.

In our earlier studies, we have shown that the average efficiency of the 3-gene knockdown method is 85-100%.[19] Thus, even though there is this variability since in all cases it has been greater than (>) 85%, we believe the knockdowns of CBRPs should follow similar efficiencies. In the worst-case scenario, if the knockdown efficiency is <85%, we might miss identifying a target gene. In fact, this problem is inherent to the screening procedures. However, when the positives are identified at the protein level indirectly by the functional evaluation, such as prolongation of TTO, they are invariably due to high knockdown efficiencies. In this study, we did not demonstrate the change in Tfpia levels as a function of the change in transcription of tfpia. It must be noted that even with human plasma, it has been very difficult to identify TFPI with antibodies. Thus, with only a limited amount of plasma that is obtained from zebrafish, it is difficult to show the changes of Tfpia expression at the protein level. The development of more sensitive methods to detect Tfpia may resolve this issue.

Since TFPI is produced from megakaryocytes, endothelium, monocytes, and smooth muscle cells, our transcription analysis may represent regulation of tfpia from all these cells. This is possible because we used RNA from the liver and spleen that carry all the above cell types.

Earlier studies have been shown that UNC6852 is a chemical degrader for PRC2 complex affecting SUZ12 and thereby affecting methyltransferase activity.[30] Our results showing increased transcription of tfpia in adult zebrafish and also prolonged TTO in the larvae when their blood vessels were injured by the laser, in the presence of UNC6852 are consistent with our knockdown data of suz12b. This is because increased levels of tfpia may increase the anticoagulant activity and thus, lead to prolonged TTO. These results provide the basis for using drugs like UNC6852 that control tfpia in an epigenetic manner and offer a novel antithrombotic target. Interestingly, estrogen-treated individuals, patients with breast cancer and lung cancer have reduced levels of TFPI and exhibited venous thrombosis.[31 32 33 34] Thus, the above drug target would be a viable alternative to prevent thrombotic episodes in these patients.

Summary

Our results demonstrate that proteins encoded by brd7, ing2, ing3, ing4, and suz12b are negatively regulating tfpia gene transcription and the reduction in their gene expression led to increased tfpia mRNA levels. Also, it led to prolonged clotting time and thus, giving a bleeding tendency. UNC6852 also produced this bleeding phenotype. Thus, our approach could be used to design novel proteolytic drugs that enhance TFPI levels via inhibiting the epigenetic proteins in treating patients with thrombotic risk. Moreover, our approach could be used to study the regulation of other proteins including coagulation factors and other plasma proteins.

Figure Legends

FIG. 1: Levels of tfpia mRNA in a primary knockdown screen of Chromatin Binding and Regulatory Proteins. Quantitative real-time PCR showing the fold change of tfpia gene expression in liver and spleen in 23 sets (Set 1-Set 23) of Chromatin Binding and Regulatory Protein-knockdowns compared to daily wild-type (WT) controls using one-way ANOVA. The bar graphs represent daily wild-type controls (squared bars), and all knockdowns (open bars and dotted bars) to the right of each wild-type were performed on the same day. Error bars represent mean±SD. Six fish were used for each set of Chromatin Binding and Regulatory Protein-knockdown and control experiments (N=6). The lines on the top represent a significant difference between wild-type and knockdown sample sets. * and *** represent p≤0.05 and p≤0.001, respectively. p-value<0.05 was considered significant.

FIG. 2: Levels of tfpia mRNA in a secondary knockdown screen of Chromatin Binding and Regulatory Proteins. Quantitative real-time PCR showing the fold change of tfpia gene expression in liver and spleen in knockdown of 9 Chromatin Binding and Regulatory Protein genes, brd7, brd9, ccdc61, ing2, ing3, ing4, supt16h, suz12a, and suz12b, with daily wild-type (WT) controls using one-way ANOVA. The bar graphs represent daily wild-type controls (squared bars), and all knockdowns (open bars and dotted bars) to the right of each wild-type were performed on the same day. Error bars represent mean±SD. Six fish were used for each of the Chromatin Binding and Regulatory Protein gene knockdown and control experiments (N=6). The lines on the top represent a significant difference between wild-type and knockdown samples. * and** represent p≤0.05 and p≤0.01, respectively. p-value<0.05 was considered significant.

FIG. 3: Tertiary knockdown screen of genes obtained from the secondary knockdown screen in adults as well as in larvae. A. Quantitative real-time PCR showing the fold change of tfpia gene expression in liver and spleen in knockdown of 5 Chromatin Binding and Regulatory Protein genes, brd7, ing2, ing3, ing4, and suz12b, with daily wild-type (WT) controls using one-way ANOVA. The bar graphs represent a wild-type control (squared bars) and knockdowns (dotted bars) that were performed on the same day. Error bars represent mean±SD. Six fish were used for each of the Chromatin Binding and Regulatory Protein gene knockdown and control experiments (N=6); B. Comparison of time to occlusion of the caudal vein after laser injury between wild-type control 5 dpf larvae and brd7, ing2, ing3, ing4, and suz12b knockdown larvae by one-way ANOVA. The dot plots represent wild-type larvae (closed circles) and the knockdown larvae (closed triangles). Error bars represent mean±SD. For experiments in A and B, p-value<0.05 was considered significant, and 50 larvae each were used in control and knockdown experiments (N=50). The lines on the top represent a significant difference between wild-type and knockdown samples. *, , * and **** represent p≤0.05, p≤0.01, p≤0.001 and p≤0.0001, respectively.

FIG. 4: Simultaneous 5-gene knockdowns in adults and larvae. A. Quantitative real-time PCR showing the fold change of tfpia gene expression in liver and spleen in simultaneous knockdown of 5 Chromatin Binding and Regulatory Protein genes, (brd7+ing2+ing3+ing4+suz12b) with wild-type (WT) controls using student's t-test. The bar graphs represent wild-type control (squared bar) and simultaneous 5-gene knockdown (dotted bar). Error bars represent mean±SD. Six fish were used for each of the simultaneous 5-gene knockdown and control experiments (N=6); B. Comparison of time to occlusion of the caudal vein after laser injury between wild-type control 5 dpf larvae and simultaneous 5-gene knockdown larvae (brd7+ing2+ing3+ing4+suz12b) by student's t-test. The dot plots represent wild-type larvae (closed circles) and the knockdown larvae (closed triangles). Error bars represent mean±SD. For experiments in A and B, p-value<0.05 was considered significant, and 50 larvae each were used in control and knockdown experiments (N=50). The lines on the top represent a significant difference between wild-type and knockdown samples. * and **** represent p≤0.05 and p≤0.0001, respectively.

FIG. 5: Treatment of zebrafish larvae and adult with a PRC2 inhibitor, UNC6852. A. Comparison of time to occlusion of the caudal vein after laser injury between wild-type control 5 dpf larvae and UNC6852-injected larvae by one-way ANOVA. The x-axis represents four different concentrations of the UNC6852 (0.075 mM, 0.15 mM, 0.3 mM and 0.6 mM) used for larval injections. The dot plots represent wild-type larvae (closed circles) and the knockdown larvae (closed triangles). Error bars represent mean±SD. 50 larvae each were used in control and UNC6852 injections (N=50); B. Quantitative real-time PCR showing the fold change of tfpia gene expression in liver and spleen for UNC6852-injected adult zebrafish with wild-type control by student's t-test. The concentration of UNC6852 used for adult injections (0.6 mM) is indicated beneath the bar graph. Error bars represent mean±SD. Six fish were used for each of the simultaneous 5-gene knockdown and control experiments (N=6). * and ** represent p≤0.001 and p≤0.0001, respectively.

REFERENCES

1. Girard T J, et al., Functional significance of the kunitz-type inhibitory domains of lipoprotein-associated coagulation inhibitor. *Nature*. 1989; 338(6215):518-520.
2. Novotny W F, et al., Purification and characterization of the lipoprotein-associated coagulation inhibitor from human plasma. *J Biol Chem*. 1989; 264(31):18832-18837.
3. Wun T C, et al., Cloning and characterization of a cDNA coding for the lipoprotein-associated coagulation inhibitor shows that it consists of three tandem kunitz-type inhibitory domains. *J Biol Chem*. 1988; 263(13):6001-6004.
4. van der Logt, et al., Intron-exon organization of the human gene coding for the lipoprotein-associated coagulation inhibitor: The factor xa dependent inhibitor of the extrinsic pathway of coagulation. *Biochemistry*. 1991; 30(6):1571-1577.
5. Bajaj M S, et al., Cultured normal human hepatocytes do not synthesize lipoprotein-associated coagulation inhibitor: Evidence that endothelium is the principal site of its synthesis. *Proc Natl Acad Sci USA*. 1990; 87(22):8869-8873.
6. Maroney S A, et al. Temporal expression of alternatively spliced forms of tissue factor pathway inhibitor in mice. *J Thromb Haemost*. 2009; 7(7):1106-1113.
7. Maroney S A, et al. Active tissue factor pathway inhibitor is expressed on the surface of coated platelets. *Blood*. 2007; 109(5):1931-1937.
8. Novotny W F, et al., Platelets secrete a coagulation inhibitor functionally and antigenically similar to the lipoprotein associated coagulation inhibitor. *Blood*. 1988; 72(6):2020-2025.
9. Bajaj M S, et al., Synthesis and expression of tissue factor pathway inhibitor by serum-stimulated fibroblasts, vascular smooth muscle cells and cardiac myocytes. *Thromb Haemost*. 1999; 82(6):1663-1672.
10. Caplice N M, et al., Expression of tissue factor pathway inhibitor in vascular smooth muscle cells and its regulation by growth factors. *Circ Res*. 1998; 83(12):1264-1270.
11. Caplice Noel M, et al., Presence of tissue factor pathway inhibitor in human atherosclerotic plaques is associated with reduced tissue factor activity. *Circulation*. 1998; 98(11):1051-1057.
12. Osterud B, et al., Sites of tissue factor pathway inhibitor (TFPI) and tissue factor expression under physiologic and pathologic conditions. on behalf of the subcommittee on tissue factor pathway inhibitor (TFPI) of the scientific and standardization committee of the ISTH. *Thromb Haemost*. 1995; 73(5):873-875.
13. Petit L, et al., Tissue factor pathway inhibitor is expressed by human monocyte-derived macrophages: Relationship to tissue factor induction by cholesterol and oxidized LDL. *Arterioscler Thromb Vasc Biol*. 1999; 19(2):309-315.
14. Skretting G, et al. Transcription factor FOXP3: A repressor of the TFPI gene? *J Cell Biochem*. 2019.
15. Luo C, et al. ADTRP regulates TFPI expression via transcription factor POU1F1 involved in coronary artery disease. *Gene*. 2020; 753:144805.
16. Jin H, et al. Physiological testosterone stimulates tissue plasminogen activator and tissue factor pathway inhibitor and inhibits plasminogen activator inhibitor type 1 release in endothelial cells. *Biochem Cell Biol*. 2007; 85(2):246-251.
17. Lupu C, et al., Novel protein ADTRP regulates TFPI expression and function in human endothelial cells in normal conditions and in response to androgen. *Blood*. 2011; 118(16):4463-4471.
18. Arroyo A, B., et al. Regulation of TFPIα expression by miR-27a/b-3p in human endothelial cells under normal conditions and in response to androgens. *Scientific Reports*. 2017; 7(1):43500.
19. Raman R, et al., RNaseH-mediated simultaneous piggyback knockdown of multiple genes in adult zebrafish. *Scientific Reports*. 2020; 10(1):20187.
20. Kim S, et al., Vivo-morpholino knockdown of alphaIIb: A novel approach to inhibit thrombocyte function in adult zebrafish. *Blood Cells Mol Dis*. 2010; 44(3):169-174.
21. Gregory M, v Selective labeling of zebrafish thrombocytes: Quantitation of thrombocyte function and detection during development. *Blood Cells, Molecules, and Diseases*. 2002; 28(3):418-427.
22. Jagadeeswaran P, et al., Laser-induced thrombosis in zebrafish. *Methods Cell Biol*. 2011; 101:197-203.
23. Harte M T, et al. BRD7, a subunit of SWI/SNF complexes, binds directly to BRCA1 and regulates BRCA1-dependent transcription. *Cancer Res*. 2010; 70(6):2538-2547.
24. Kikuchi M, et al. TRIM24 mediates ligand-dependent activation of androgen receptor and is repressed by a bromodomain-containing protein, BRD7, in prostate cancer cells. *Biochim Biophys Acta*. 2009; 1793(12):1828-1836.
25. Peng C, et al. The transcriptional regulation role of BRD7 by binding to acetylated histone through bromodomain. *J Cell Biochem*. 2006; 97(4):882-892.
26. Coles A H, et al., The ING gene family in the regulation of cell growth and tumorigenesis. *J Cell Physiol*. 2009; 218(1):45-57.
27. Menéndez C, et al., ING proteins in cellular senescence. *Curr Drug Targets*. 2009; 10(5):406-417.
28. Margueron R, Reinberg D. The polycomb complex PRC2 and its mark in life. *Nature*. 2011; 469(7330):343-349.
29. Yu J, et al. Reduced H3K27me3 leads to abnormal hox gene expression in neural tube defects. *Epigenetics Chromatin*. 2019; 12(1):76-1.

30. Potjewyd F, Turner A W, Beri J, et al. Degradation of polycomb repressive complex 2 with an EED-targeted bivalent chemical degrader. *Cell chemical biology.* 2020; 27(1):47-56.e15.
31. Dahm A E, et al., Estrogens, selective estrogen receptor modulators, and a selective estrogen receptor down-regulator inhibit endothelial production of tissue factor pathway inhibitor 1. *BMC Cardiovasc Disord.* 2006; 6:40-40.
32. Ali Ho, et al., Oestrogen induced downregulation of TFPI expression is mediated by ERα. *Thromb Res.* 2014; 134(1):138-143.
33. Rhone P, et al. Comprehensive analysis of haemostatic profile depending on clinicopathological determinants in breast cancer patients. *Biosci Rep.* 2018; 38(2): BSR20171657.
34. Fei X, et al., Tissue factor pathway inhibitor-1 is a valuable marker for the prediction of deep venous thrombosis and tumor metastasis in patients with lung cancer. *Biomed Res Int.* 2017; 2017:8983763.

A number of embodiments of the invention have been described. Nevertheless, it can be understood that various modifications may be made without departing from the spirit and scope of the invention. Accordingly, other embodiments are within the scope of the following claims.

What is claimed is:

1. A method for decreasing the risk of, or preventing, a thrombotic event or a thrombosis in an individual in need thereof, comprising administering to the individual in need thereof a compound having a formula:

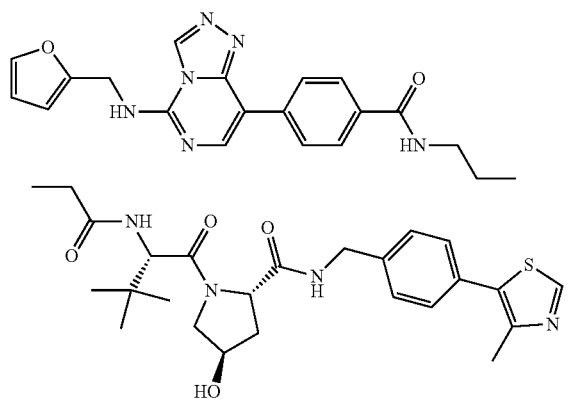

or a salt, hydrate, solvate, tautomer, stereoisomer or deuterated isoform thereof,
wherein the compound or the salt, hydrate, solvate, tautomer, stereoisomer or deuterated isoform thereof is administered to an individual in need thereof receiving estrogen treatment.

2. The method of claim 1, wherein the compound is formulated or manufactured as a parenteral formulation.

3. The method of claim 1, wherein the compound is formulated in a unit dosage amount ranging from between 0.1 mg to about 1 gram.

4. The method of claim 2, wherein the thrombosis is a venous thrombosis.

5. The method of claim 1, wherein the compound is formulated or manufactured as: an aqueous solution, a liposome, an injectable solution, a freeze-dried powder, a feed, a food, a food supplement, a pellet, a liquid, an elixir, an aerosol, an inhalant, an adhesive, a spray, a powder, a freeze-dried powder, a patch, a tablet, a pill, a capsule, a gel, a geltab, a lozenge, a caplet, a nanosuspension, a nanoparticle, a nanoliposome, a microgel or a suppository.

6. The method of claim 1, wherein the compound is formulated as an immediate release formulation or a controlled release formulation.

7. The method of claim 1, wherein the individual in need thereof is a patient with a cancer.

8. The method of claim 7, wherein the cancer is a breast cancer or a lung cancer.

9. A method for decreasing the risk of a thrombotic event or a thrombosis in an individual in need thereof, comprising administering to the individual in need thereof a compound having a formula:

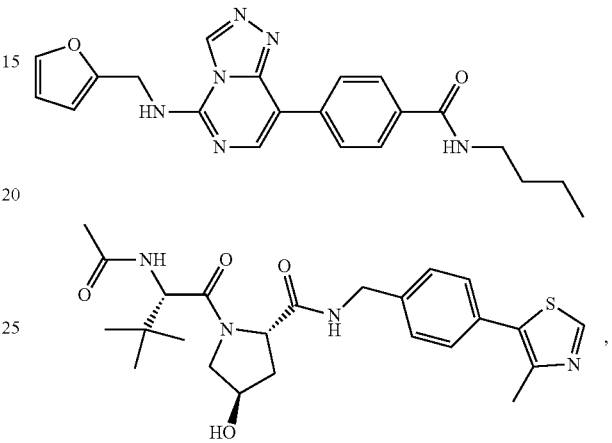

or a salt, hydrate, solvate, tautomer, stereoisomer or deuterated isoform thereof,
wherein the compound or the salt, hydrate, solvate, tautomer, stereoisomer or deuterated isoform thereof is administered to an individual in need thereof receiving estrogen treatment.

10. The method of claim 1, wherein the compound is formulated or manufactured as an aqueous solution, a liposome, an injectable solution, a tablet, a pill, a lozenge, a capsule, a caplet, a spray, a sachet, a powder, a freeze-dried powder, an inhalant, a patch, a gel, a geltab, a nanosuspension, a nanoparticle, a nanoliposome, a microgel, a pellet, a suppository or any combination thereof.

* * * * *

```
                         SEQUENCE LISTING

Sequence total quantity: 6
SEQ ID NO: 1            moltype = DNA  length = 15
FEATURE                 Location/Qualifiers
misc_feature            1..15
                        note = Synthetic
source                  1..15
                        mol_type = other DNA
                        organism = synthetic construct
SEQUENCE: 1
tataaattgt aactg                                                         15

SEQ ID NO: 2            moltype = DNA  length = 25
FEATURE                 Location/Qualifiers
misc_feature            1..25
                        note = Synthetic
source                  1..25
                        mol_type = other DNA
                        organism = synthetic construct
SEQUENCE: 2
cctcttacct cagttacaat ttata                                              25

SEQ ID NO: 3            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 3
ctcccaacca gctaaacagg                                                    20

SEQ ID NO: 4            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 4
gcgaaagact tgacatctgc                                                    20

SEQ ID NO: 5            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 5
tctcttgctc cttccaccat                                                    20

SEQ ID NO: 6            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 6
catcgtactc ctgcttgctg                                                    20
```